United States Patent
Boatman et al.

(10) Patent No.: US 11,628,138 B2
(45) Date of Patent: *Apr. 18, 2023

(54) STEROIDAL COMPOSITIONS AND METHOD OF MAKING AND USE

(71) Applicant: FARMAKEIO OUTSOURCING, LLC, Southlake, TX (US)

(72) Inventors: Cody Boatman, Greenville, TX (US); Daniel DeNeui, Colleyville, TX (US); Justin Graves, Southlake, TX (US)

(73) Assignee: FARMAKEIO OUTSOURCING LLC, Southlake, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/730,305

(22) Filed: Apr. 27, 2022

(65) Prior Publication Data

US 2022/0249367 A1 Aug. 11, 2022

Related U.S. Application Data

(63) Continuation of application No. 17/204,217, filed on Mar. 17, 2021, now abandoned, which is a continuation of application No. 17/162,549, filed on Jan. 29, 2021, now abandoned.

(60) Provisional application No. 62/967,312, filed on Jan. 29, 2020.

(51) Int. Cl.
| | |
|---|---|
| *A61K 9/00* | (2006.01) |
| *A61K 9/20* | (2006.01) |
| *A61K 9/28* | (2006.01) |
| *A61K 31/568* | (2006.01) |
| *A61K 31/573* | (2006.01) |

(52) U.S. Cl.
CPC .......... *A61K 9/0024* (2013.01); *A61K 9/2054* (2013.01); *A61K 9/282* (2013.01); *A61K 31/568* (2013.01); *A61K 31/573* (2013.01)

(58) Field of Classification Search
CPC .... A61K 9/0024; A61K 9/2054; A61K 9/282; A61K 31/568; A61K 31/573
See application file for complete search history.

(56) References Cited

U.S. PATENT DOCUMENTS

| | | | |
|---|---|---|---|
| 4,393,041 | A | 7/1983 | Brown et al. |
| 2004/0002482 | A1 | 1/2004 | Dudley et al. |
| 2004/0141925 | A1 | 7/2004 | Bosch et al. |
| 2006/0252049 | A1 | 11/2006 | Shuler et al. |
| 2008/0044476 | A1 | 2/2008 | Lyons et al. |
| 2011/0244043 | A1 | 10/2011 | Xu et al. |
| 2020/0071415 | A1 | 3/2020 | Cronier et al. |
| 2021/0228479 | A1 | 7/2021 | Boatman et al. |
| 2021/0236419 | A1 | 8/2021 | Boatman et al. |

OTHER PUBLICATIONS

CMP Pharma Announcement dated Mar. 5, 2015.
Jordan Jr., John P. "Allergy and Topical Irritation Associated With Transdermal Testosterone Administration: A Comparison of Scrotal and Nonscrotal Transdermal Systems," American Journal of Contact Dermatitis, vol. 8, No. 2 Jun. 1997, pp. 108-113.
Wilson, Douglas E. et al., "Use of Topical Corticosteroid Pretreatment to Reduce the Incidence and Severity of Skin Reactions Associated with Testosterone Transdermal Therapy," Clinical Therapeutics, vol. 20, No. 2, 1998.
Deneui, Terri, et al. "Subcutaneous Testosterone Pellet Implants: Understanding the Role of Triamcinolone" Winter 2018.
McCullough, Andrew, "A Review of Testosterone Pellets in the Treatment of Hypogonadism," Curr. Sex Health Rep. (2014) 6:265-269.
Manica, Lucas A. Heldt, et al., "Testosterone Pellet Associated Dermititis: Report and Review of Testopel-Related Cutaneous Adverse Effects," Cueus 9(8): e 1560.
Cavender, Richard K., et al., "Subcutaneous Testosterone Pellet Implant (Testopel) Therapy for Men with Testosterone Deficiency Syndrome: A Single-Site Retrospective Safety Analysis." J.Sex Med 2009; 6:3177-3192.
Endo Pharmaceuticals, Inc. "Testopel"—testosterone pellet disclosure.
Ference, Jonathan D., et al, "Choosing Topical Corticosteroids," Am Family Physician, Jan. 15, 2009, vol. 79, No. 2, 135-140.
National Institutes of Health MedlinePlus. "Hydrocotrisone Topical" Jun. 28, 2021.
Shah, Alkil B. et al., "A Foreign Body Reaction to a Contraceptive Implant," J. Womens Health Gynecol 2014,vol. 1.
Beardwell, Ann: "Subcutaneous Atrophy after Local Corticosteroid Injection," Brit. med. J., 1967, 3, 600.
Conners, William et al., "Outcomes with the "V" Implantation Technique vs. Standard Technique for Testosterone Pellet Therapy," J Sex Med 2011;8:3465-3470.
EHealthline Will you have Soft tissue necrosis with Kenalog—from FDA report. https://www.ehealthme.com/ds/kenalog/soft-tissue- necrosis.
Fisherman, Elmer W.; et al., "Local Subcutaneous Atrophy," J.A.M.A., Mar. 24, 1962.
Hanasono, Matthew M. et al., "Correction of the Soft Tissue Polybeak Using Triamcinolone Injection," Arch Facial Plast Surg. 2002;4:26-30.
Hayward, William A. et al., "Intralesional Injection of Triamcinolone Acetonide for subcutaneous Lipoma causing Musculoskeletal and Neurologic Symptoms," J Clin Aesthet Dermatol. 2018; 11(5):38-42.
Kanbe, Katsuaki, et al, "Simultaneous Treatment with Subcutaneous Injection of Galimumab and Intra-articular Injection of Triamcinolone Acetonide (K-Method) in Patients with Rheumatoid Arthritis Undergoing Switching of Biologies: Retrospective Case-Control Study," Clinical Medicine Insights: Arthritis and Musculoskeletal Disorders, 2016:9 45-49.

(Continued)

*Primary Examiner* — Kyung S Chang
(74) *Attorney, Agent, or Firm* — Fisherbroyles, LLP; Anthony Dovale; Richard Echler

(57) ABSTRACT

Disclosed herein are compositions useful for treating hypogonadism in men and women. The disclosed compositions comprise an admixture of testosterone and triamcinolone which combination alleviates pellet injection site pain and/or discomfort, as well as pellet extrusion.

22 Claims, No Drawings

(56) References Cited

OTHER PUBLICATIONS

Kelleher, S. et al., "Extrusion of testosterone pellets: a randomized controlled clinical study," Clinical Endocrinology, 51, 469-471.

Kelleher, S. et al., "Influence of implantation site and track geometry on the extrusion rate and pharmacology of testosterone implants," Clinical Endocrinology, 55, 531-536.

Martins, Nadia et al., "Treatment of Persistent Cutaneous Atrophy After Corticosteroid Injection with Fat Graft," Reumatol Clin. 2017.

McMahon, Chris G., et al., "Pharmacokinetics, Clinical Efficacy, Safety Profile, and Patient-Reported Outcomes in Patients Receiving Subcutaneous Testosterone Pellets 900 mg for Treatment of Symptoms Associated With Androgen Deficiency," J Sex Med 2017;14:883-890.

Neal, Danielle, et al., "Serpiginous hypopigmentation secondary to intra-articular corticosteroid injection," Dermatology Online Journal, 23(4).

Ni, Jiaxiang, et al., "Subcutaneous Injection of Triamcinolone and Lidocaine to Prevent Postherpetic Neuralgia," Pain Physician 2017;20:397-403.

Pace, Collier S., et al., "Soft Tissue Atrophy Related to Corticosteroid Injection" Review of the Literature and Implications for Hand Surgeons, J Hand Surg Am. 2018;43(6):558-563.

Pariser, Harry, et al., "Intralesional Injections of Triamcinolone, Effects of Different Concentrations on Psoriatic Lesions," Archives of Dermatology, vol. 87, Feb. 1963; 97-96.

Park, Sun-Kyung, et al., "Hypopigmentation and subcutaneous fat, muscle atrophy after local corticosteroid injection," Korean J Anesthesiol Dec. 2013 65(6 Suppl):S59-S61.

Wu, Douglas C., et al., "Randomized, Double-Blinded, Sham-Controlled, Split—=Hand Trial Evaluating the Safety and Efficacy of Triamcinolone Acetate Injection After Calcium Hydroxyapatite Volume Restoration," Dermatol; Surg 2018;4;534-541.

Zacharin, M. R., et al., "Treatment of hypogonadal adolescent boys with long acting subcutaneous testosterone pellets," Archives of Disease in Childhood 1997;76:495-499.

STEROIDAL COMPOSITIONS AND METHOD OF MAKING AND USE

PRIORITY

This Application claims priority to U.S. application Ser. No. 17/204,217, filed Mar. 17, 2021, which claims priority to U.S. application Ser. No. 17/162,549, filed Jan. 29, 2021, which claims priority to U.S. Provisional Application Ser. No. 62/967,312, filed Jan. 29, 2020, all of which are incorporated by reference herein in their entirety.

FIELD

Disclosed herein are compositions suitable for use in increasing the energy level, memory function and cognitive focus, and lowering the feeling of lethargy in men and women. Further disclosed are methods of use and processes for preparing the disclosed compositions.

DETAILED DESCRIPTION

The materials, compounds, compositions, articles, methods, and processes described herein may be understood more readily by reference to the following detailed description of specific aspects of the disclosed subject matter and the Examples included therein.

Also, throughout this specification, various publications are referenced. The disclosures of these publications in their entireties are hereby incorporated by reference into this application in order to more fully describe the state of the art to which the disclosed matter pertains. The references disclosed are also individually and specifically incorporated by reference herein for the material contained in them that is discussed in the sentence in which the reference is relied upon.

General Definitions

In this specification and in the claims that follow, reference will be made to a number of terms, which shall be defined to have the following meanings:
All percentages, ratios and proportions herein are by weight, unless otherwise specified. All temperatures are in degrees Celsius (° C.) unless otherwise specified.

A weight percent of a component, unless specifically stated to the contrary, is based on the total weight of the formulation or composition in which the component is included.

By "effective amount" as used herein means "an amount of one or more of the disclosed compounds, effective at dosages and for periods of time necessary to achieve the desired or therapeutic result." An effective amount may vary according to factors known in the art, such as the disease state, age, sex, and weight of the human or animal being treated. Although particular dosage regimes may be described in examples herein, a person skilled in the art would appreciate that the dosage regime may be altered to provide optimum therapeutic response. For example, the amount of the disclosed compositions in each doses can be administered in a frequency determine by measurement of the testosterone levels in a subject.

"Admixture" or "blend" is generally used herein means a physical combination of two or more different components "Excipient" is used herein to include any other compound that may be contained in or combined with one or more of the disclosed inhibitors that is not a therapeutically or biologically active compound. As such, an excipient should be pharmaceutically or biologically acceptable or relevant (for example, an excipient should generally be non-toxic to the subject). "Excipient" includes a single such compound and is also intended to include a plurality of excipients.

As used herein, the term "subject" refers to a human or an animal that has been diagnosed with insufficient testosterone levels. The threshold level for the condition of "low testosterone" is based upon the subject to be treated and other medical conditions can influence the course of treatment.

The term "treat" or other forms of the word such as "treated" or "treatment" is used herein to mean that administration of a the disclosed compositions to a subject identified as having a need for testosterone therapy.

Throughout the description and claims of this specification the word "comprise" and other forms of the word, such as "comprising" and "comprises," means including but not limited to, and is not intended to exclude, for example, other additives, components, integers, or steps.

As used in the description and the appended claims, the singular forms "a," "an," and "the" include plural referents unless the context clearly dictates otherwise. Thus, for example, reference to "a composition" includes mixtures of two or more such compositions, reference to "a chemotherapeutic agent" includes mixtures of two or more such chemotherapeutic agents, reference to "the compound" includes mixtures of two or more such compounds, for example, salts thereof, and the like.

"Optional" or "optionally" means that the subsequently described event or circumstance can or cannot occur, and that the description includes instances where the event or circumstance occurs and instances where it does not.

Ranges can be expressed herein as from "about" one particular value, and/or to "about" another particular value. When such a range is expressed, another aspect includes from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. It is also understood that when a value is disclosed, then "less than or equal to" the value, "greater than or equal to the value," and possible ranges between values are also disclosed, as appropriately understood by the skilled artisan. For example, if the value "10" is disclosed, then "less than or equal to 10" as well as "greater than or equal to 10" is also disclosed. It is also understood that throughout the application data are provided in a number of different formats and that this data represent endpoints and starting points and ranges for any combination of the data points. For example, if a particular data point "10" and a particular data point "15" are disclosed, it is understood that greater than, greater than or equal to, less than, less than or equal to, and equal to 10 and 15 are considered disclosed as well as between 10 and 15. It is also understood that each unit between two particular units are also disclosed. For example, if 10 and 15 are disclosed, then 11, 12, 13, and 14 are also disclosed.

As used herein, "pharmaceutically acceptable" means physiologically tolerable, for either human or veterinary applications. In addition, "pharmaceutically acceptable" is meant a material that is not biologically or otherwise undesirable, i.e., the material may be administered to a subject without causing any undesirable biological effects or interacting in a deleterious manner with any of the other components of the pharmaceutical composition in which it is contained. Essentially, the pharmaceutically acceptable material is nontoxic to the recipient. The carrier would naturally be selected to minimize any degradation of the active ingredient and to minimize any adverse side effects in the subject, as would be well known to one of skill in the art. For a discussion of pharmaceutically acceptable carriers and other components of pharmaceutical compositions, see, e.g., Remington's Pharmaceutical Sciences, 18th ed., Mack Publishing Company, 1990.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the described invention, the preferred methods and materials are now described. All publications mentioned herein are incorporated herein by reference to disclose and describe the methods and/or materials in connection with which the publications are cited.

Details associated with the embodiments described above and others are described below.

Testosterone is the primary male sex hormone and an anabolic steroid. In male humans, testosterone plays a key role in the development of male reproductive tissues such as testes and prostate, as well as promoting secondary sexual characteristics such as increase muscle and bone mass, and the growth of body hair. In addition, testosterone is involved in health and well-being, and the prevention of osteoporosis. Insufficient levels of testosterone in men my lead to abnormalities including frailty and bone loss.

Although testosterone is considered a male sex hormone, women produce small amounts of testosterone in their ovaries and adrenal glands. Together with the female sex hormone estrogen, testosterone plays a role in the growth and maintenance of female reproductive tissue and bone mass.

Without wishing to be limited by theory, clinicians recognize that testosterone is present in the body in 3 forms: free testosterone, albumin-bound testosterone, and testosterone bound to sex hormone-binding globulin (SHBG). In young healthy men, only 1% to 2% of testosterone is free, about 40% is albumin-bound and readily dissociates to free testosterone, and the remainder is tightly bound to SHBG, which does not readily dissociate and is therefore biologically unavailable (see, Kaufman J et al., "The decline of androgen levels in elderly men and its clinical and therapeutic implications." *Endocr Rev.* 2005; 26:833-876). The amount of SHBG increases with age, decreasing the amount of bioavailable testosterone. Serum levels of testosterone remain approximately stable until about age 40. After age 40, total levels of testosterone decrease by 1% to 2% annually, and serum free testosterone levels decrease by 2% to 3% annually.

Delivery of implantable pharmaceutical compositions in the form of pellets is a long established practice. One drawback of subcutaneous administration of implantable pellets is the irritation, soreness, and inflammation which occurs at the injection site. The disclosed compositions overcome this drawback. Without wishing to be limited by theory, the inclusion of triamcinolone in the disclosed compositions overcomes the adverse effects of subcutaneous pellet injection.

Compositions

Disclosed herein are implantable pharmaceutical compositions, comprising:
a) from about 90% to about 99% by weight of testosterone;
b) from about 0.005% to about 0.05% by weight of triamcinolone;
c) the balance carriers and adjunct ingredients.

In one aspect the compositions comprise from about 90% to about 99% by weight of testosterone. In one embodiment the composition comprises from about 92% to about 99% by weight of testosterone. In a further embodiment the composition comprises from about 90% to about 97% by weight of testosterone. In another embodiment the composition comprises from about 93% to about 99% by weight of testosterone. In a still further embodiment the composition comprises from about 93% to about 97% by weight of testosterone. In a yet further embodiment the composition comprises 95% by weight of testosterone. The disclosed compositions can comprise any amount from about 90% to about 99% by weight of testosterone, including fractional percentages, for example, 90%, 91%, 92%, 93%, 94%, 95%, 96%, 97%, 98% and 99%.

In another aspect the compositions comprise from about 0.005% to about 0.05% by weight of triamcinolone. In one embodiment the composition comprises from about 0.0075% to about 0.05% by weight of triamcinolone. In another embodiment the composition comprises from about 0.005% to about 0.04% by weight of triamcinolone. In a further embodiment the composition comprises from about 0.01% to about 0.04% by weight of triamcinolone. In a still further embodiment the composition comprises from about 0.015% to about 0.03% by weight of triamcinolone. In as yet further embodiment the composition comprises 0.02% by weight of triamcinolone. The disclosed compositions can comprise any amount from about 0.005% to about 0.05% by weight of triamcinolone, including fractional percentages, for example, 0.005%, 0.006%, 0.007%, 0.008%, 0.009%, 0.01%, 0.02%, 0.03%, 0.04% or 0.05%.

The disclosed compositions are in the form of a pellet. As such, the disclosed compositions can further comprise a coating agent. Disclosed herein are implantable pharmaceutical compositions, comprising:
a) from about 90% to about 99% by weight of testosterone;
b) from about 0.005% to about 0.05% by weight of triamcinolone;
c) from about 0.5% to about 9% by weight of a coating agent; and
d) the balance carriers and adjunct ingredients;
wherein the pellet has a hardness less than about 75 Newtons.

In one embodiment the hardness of the pellets require an average force of from about 50 Newtons to about 79 Newtons to fracture the pellets. Without wishing to be limited by theory, some pellets can fracture under a force of less than about 50 Newtons while other pellets can fracture under the force of less than 65 Newtons. In one embodiment, at least about 80% of the pellets fracture within 5 Newtons of the average fracture force. In a non-limiting example, pellets comprising 200 mg of testosterone and 40 μg off triamcinolone can fracture under a force of from about 50 Newtons to about 70 Newtons.

In one embodiment the compositions comprise from about 1% to about 8% by weight of a coating agent. In one embodiment the compositions comprise from about 2% to about 7% by weight of a coating agent. In one embodiment the compositions comprise from about 1% to about 5% by weight of a coating agent. In one embodiment the compositions comprise from about 3% to about 6% by weight of a coating agent. In one embodiment the compositions comprise about 4% by weight of a coating agent. The disclosed compositions can comprise any amount from about 0.5% to about 9% by weight of a coating agent, including fractional percentages, for example, 0.5%, 0.6%, 0.7%, 0.8%, 0.9%, 1%, 2%, 3%, 4%, 5%, 6%, 7%, 8%, or 9%.

Non-limiting examples of coating agents which can comprise the disclosed compositions include a coating agent chosen from dextran, poly(ε-caprolacton), poly(1,4-dioxan-2-one), poly(sebacic anhydride), poly(dodecanoic anhydride), poly(ethylene glycol), polyoxyethylene, stearic acid, stearyl alcohol, ethylene glycol palmitostearate, cetyl esters wax, poly(1,3-bis(carboxyphenoxy)propane-co-sebacic acid), poly(3-hydroxybutyrate-co-3-hydroxyvalerate) or a combination thereof. In one embodiment the coating agent is stearic acid or stearyl alcohol. In one non-limiting example from about 0.005% to about 0.05% by weight of triamcinolone.

The disclosed compositions can further comprise from about 0.5% to about 1.5% by weight of a binding agent. In one non-limiting example, the composition comprises 1% by weight of a binding agent. Non-limiting examples of binding agents which the disclosed compositions can comprise include a binding agent is chosen from polyethylene glycol 1500, polyethylene glycol 2000, polyethylene glycol 3000, polyethylene glycol 4000, polyethylene glycol 6000, polyethylene glycol 8000, polyethylene glycol 10000, methylcellulose, ethylcellulose, hydroxymethyl cellulose, hydroxyethylcellulose, hydroxypropyl methylcellulose, polyoxyethylene, copolymers of polyoxyethylene-polyoxypropylene and mixtures thereof. In one embodiment binding agent is methylcellulose, ethylcellulose, hydroxymethyl cellulose, or hydroxyethylcellulose. In one non-limiting example, binding agent is ethylcellulose.

The Disclosed Composition

Another aspect of the disclosed implantable pharmaceutical composition are pellets, comprising:
a) from about 10 mg to about 250 mg by weight of testosterone;
b) from about 1 µg to about 50 µg by weight of triamcinolone; and
c) from about 0.5 mg to about 12.5 mg by weight of one or more adjunct ingredients or carriers.

In one embodiment the pellets comprise 12.5 mg by weight of testosterone and 2.5 µg of triamcinolone. In a further embodiment the pellets comprise 25 mg by weight of testosterone and 5 µg of triamcinolone. In another embodiment the pellets comprise 25 mg by weight of testosterone and 5 µg of triamcinolone. In a still further embodiment the pellets comprise 37.5 mg by weight of testosterone and 7.5 µg of triamcinolone. In a yet further embodiment the pellets comprise 50 mg by weight of testosterone and 10 µg of triamcinolone. In a still yet further embodiment the pellets comprise 62.5 mg by weight of testosterone and 2.5 µg of triamcinolone. In a still another embodiment the pellets comprise 87.5 mg by weight of testosterone and 17.5 µg of triamcinolone. In a yet another embodiment the pellets comprise 100 mg by weight of testosterone and 20 µg of triamcinolone. In still yet another embodiment the pellets comprise 200 mg by weight of testosterone and 40 µg of triamcinolone. The disclosed compositions can comprise any amount of testosterone and triamcinolone from about 200 mg by weight of testosterone and 40 µg of triamcinolone and from about 1 µg to about 50 µg by weight of triamcinolone.

In a further aspect, the composition comprises a ratio of 5000:1 testosterone to triamcinolone. In a further aspect, the composition comprises a ratio of 5000:1 testosterone to triamcinolone. In a further embodiment of this aspect, the composition comprises a ratio of 4500:1 testosterone to triamcinolone. In another embodiment of this aspect, the composition comprises a ratio of 5500:1 testosterone to triamcinolone. In a yet further embodiment of this aspect, the composition comprises a ratio of 5000:1.1 testosterone to triamcinolone. In a still further embodiment of this aspect, the composition comprises a ratio of 5000:0.9 testosterone to triamcinolone.

The disclosed compositions of this aspect can comprise from about 0.4 mg to about 12 mg by weight of a coating agent. Non-limiting examples of coating agents which can comprise the disclosed compositions include a coating agent chosen from dextran, poly(ε-caprolacton), poly(1,4-dioxan-2-one), poly(sebacic anhydride), poly(dodecanoic anhydride), poly(ethylene glycol), polyoxyethylene, stearic acid, stearyl alcohol, ethylene glycol palmitostearate, cetyl esters wax, poly(1,3-bis(carboxyphenoxy)propane-co-sebacic acid), poly(3-hydroxybutyrate-co-3-hydroxyvalerate) or a combination thereof. In one embodiment the coating agent is stearic acid or stearyl alcohol. In one embodiment the coating agent is stearic acid or stearyl alcohol. In one non-limiting example the coating agent comprises 4% by weight of stearic acid.

The disclosed compositions of this aspect can comprise a binding agent. Non-limiting examples of binding agents suitable for use in the disclosed compositions are chosen from polyethylene glycol 1500, polyethylene glycol 2000, polyethylene glycol 3000, polyethylene glycol 4000, polyethylene glycol 6000, polyethylene glycol 8000, polyethylene glycol 10000, methylcellulose, ethylcellulose, hydroxymethyl cellulose, hydroxyethylcellulose, hydroxypropyl methylcellulose, polyoxyethylene, copolymers of polyoxyethylene-polyoxypropylene and mixtures thereof. In one embodiment the binding agent is methylcellulose, ethylcellulose, hydroxymethyl cellulose, or hydroxyethylcellulose. In one non-limiting example the binding agent is ethylcellulose.

Methods

Another aspect of the present disclosure relates to methods of treating a subject having the need for increased testosterone levels. The disclosed methods for this aspect, comprise treating a subject in need of an increased testosterone level with a composition comprising:
a) from about 90% to about 99% by weight of testosterone;
b) from about 0.005% to about 0.05% by weight of triamcinolone;
c) the balance carriers and adjunct ingredients;
wherein the compositions are described herein above.

The treatment comprises injecting an implantable pharmaceutical composition into a subject in need subcutaneously. In one aspect the composition is in the form of an implantable pellet as described herein. The pellets are inserted by a licensed medical practitioner, inter alia, MD, DO, NP, PA or NMD. The pellets comprise a sufficient amount of active ingredients, i.e., testosterone and triamcinolone that the frequency of administration is greater than one month, in one embodiment two months, in another embodiment three months, in a further embodiment four months, in a still further embodiment five months. In one non-limiting example, the treatment is from about 4 to 6 months predicated on the age, body mass, physical condition etc. of the subject.

Subjects reporting conditions associated with low testosterone presented themselves for treatment of their conditions. The subjects, 139 males and 300 females, were treated with a disclosed composition. The subjects were not told they were receiving testosterone therapy for the treatment of their conditions.

Table I below shows the initial total testosterone, initial free testosterone, final total testosterone, final free testosterone levels and the dosing for 30 representative male subjects which presented themselves to the clinic (EVEXIAS Medical Center, Southlake Tex.) with various complaints and were subsequently administered a disclosed composition.

TABLE I

| Patient No. | Initial total testosterone (ng/dL) | Initial free testosterone (ng/dL) | Pellet testosterone (mg) | Final total testosterone (ng/dL) | Final free testosterone (ng/dL) |
|---|---|---|---|---|---|
| 1 | 303 | 60.3 | 2400 | 1034 | 205 |
| 2 | 253 | 48.5 | 2400 | 929 | 253.2 |
| 3 | 270 | 52.1 | 2400 | 1421 | 225.7 |
| 4 | 380 | 64.2 | 2400 | 1017 | 202.2 |
| 5 | 674 | 196 | 1800 | 951 | 286.3 |
| 6 | 604 | 95.6 | 1800 | 1230 | 229.1 |
| 7 | 317 | 60.8 | 2400 | 1161 | 220.4 |
| 8 | 479 | 85.6 | 2400 | 994 | 194.1 |
| 9 | 317 | 60.3 | 2600 | 887 | 184.3 |
| 10 | 238 | 43 | 2800 | 1003 | 183.6 |
| 11 | 375 | 89.5 | 2400 | 1139 | 231.7 |
| 12 | 298 | 61.8 | 2400 | 957 | 192 |
| 13 | 597 | 88 | 2000 | 999 | 172.5 |
| 14 | 522 | 100.9 | 2000 | 931 | 180.7 |
| 15 | 444 | 91.8 | 2000 | 888 | 178.5 |
| 16 | 336 | 58.3 | 2400 | 968 | 188.7 |
| 17 | 331 | 71.6 | 2400 | 1103 | 183.6 |
| 18 | 271 | 57.4 | 2400 | 739 | 171.7 |
| 19 | 257 | 7 | 2600 | 17.5 | 3.6 |
| 20 | 591 | 77.8 | 1400 | 1317 | 267.3 |
| 21 | 172 | 4 | 2400 | 19.2 | 4.4 |
| 22 | 208 | 7.8 | 2800 | 1006 | 26.1 |
| 23 | 461 | 5.9 | 2000 | 1304 | 19.6 |
| 24 | 368 | 6.8 | 2400 | 1480 | 20.6 |
| 25 | 409 | 6.1 | 2400 | 1118 | 27.2 |
| 26 | 283 | 9.8 | 2600 | >1500 | 40.1 |
| 27 | 158 | 3 | 2400 | 563 | 13.7 |
| 28 | 359 | 8.8 | 2800 | 1400 | 33.2 |
| 29 | 462 | 10 | 2000 | 1459 | 23.8 |
| 30 | 272 | 11.9 | 2100 | 1037 | 33.4 |

Table II below shows the increase in the final total and free testosterone for the representative subjects. Except for subjects 5, 13 and 14 there was at least a doubling of total testosterone.

TABLE II

| Patient No. | Initial total testost. (ng/dL) | Initial free testest. (ng/dL) | Final total testost. (ng/dL) | Final free testost. (ng/dL) | increase total testosterone (final/initial) | increase free testosterone (final/initial) |
|---|---|---|---|---|---|---|
| 1 | 303 | 60.3 | 1034 | 205 | 3.4 | 3.4 |
| 2 | 253 | 48.5 | 929 | 253.2 | 3.7 | 5.2 |
| 3 | 270 | 52.1 | 1421 | 225.7 | 5.3 | 4.3 |
| 4 | 380 | 64.2 | 1017 | 202.2 | 2.7 | 3.1 |
| 5 | 674 | 196 | 951 | 286.3 | 1.4 | 1.5 |
| 6 | 604 | 95.6 | 1230 | 229.1 | 2.0 | 2.4 |
| 7 | 317 | 60.8 | 1161 | 220.4 | 3.7 | 3.6 |
| 8 | 479 | 85.6 | 994 | 194.1 | 2.1 | 2.3 |
| 9 | 317 | 60.3 | 887 | 184.3 | 2.8 | 3.1 |
| 10 | 238 | 43 | 1003 | 183.6 | 4.2 | 4.3 |
| 11 | 375 | 89.5 | 1139 | 231.7 | 3.0 | 2.6 |
| 12 | 298 | 61.8 | 957 | 192 | 3.2 | 3.1 |
| 13 | 597 | 88 | 999 | 172.5 | 1.7 | 2.0 |
| 14 | 522 | 100.9 | 931 | 180.7 | 1.7 | 1.8 |
| 15 | 444 | 91.8 | 888 | 178.5 | 2.0 | 1.9 |
| 16 | 336 | 58.3 | 968 | 188.7 | 2.9 | 3.2 |
| 17 | 331 | 71.6 | 1103 | 183.6 | 3.3 | 2.6 |
| 18 | 271 | 57.4 | 739 | 171.7 | 2.7 | 3.0 |
| 19 | 257 | 7 | 921 | 17.5 | 3.6 | 2.5 |
| 20 | 591 | 77.8 | 1317 | 267.3 | 2.2 | 3.4 |
| 21 | 172 | 4 | 758 | 19.2 | 4.4 | 4.8 |
| 22 | 208 | 7.8 | 1006 | 26.1 | 4.8 | 3.3 |
| 23 | 461 | 5.9 | 1304 | 19.6 | 2.8 | 3.3 |
| 24 | 368 | 6.8 | 1480 | 20.6 | 4.0 | 3.0 |
| 25 | 409 | 6.1 | 1118 | 27.2 | 2.7 | 4.5 |
| 26 | 283 | 9.8 | >1500 | 40.1 | >5.3 | 4.1 |
| 27 | 158 | 3 | 563 | 13.7 | 3.6 | 4.6 |
| 28 | 359 | 8.8 | 1400 | 33.2 | 3.9 | 3.8 |
| 29 | 462 | 10 | 1459 | 23.8 | 3.2 | 2.4 |
| 30 | 272 | 11.9 | 1037 | 33.4 | 3.8 | 2.9 |

Without wishing to be limited by theory, a reduced increase in total and/or free testosterone can be an indication of other pathologies, for example, obesity, diabetes, alcoholism, drug addiction and the like.

Process

Disclosed is a process for preparing an implantable pharmaceutical composition, comprising:
A) combining testosterone, 0.02% by weight of triamcinolone and a 2% by weight of a coating agent to form an admixture;
B) adding to the admixture formed in step (A) 1% by weight of a binding agent dissolved in a volatile carrier to from wet granules;
C) drying the wet granules to remove the volatile carrier to form bulk granules;
D) milling the bulk granules;
E) combining the milled granules with 2% by weight of a coating agent to form an implantable pharmaceutical composition.

The disclosed process can also optionally comprise the further step:
F) processing the implantable pharmaceutical composition into a pellet form having a consistent weight and the pellet having a hardness less than about 75 Newtons.

The following is a non-limiting example of a process for preparing the disclosed compositions. All formulation was conducted in an FDA Registered 503B Outsourcing Facility, operated by FarmaKeio Outsourcing, in Southlake, Tex.

Raw testosterone (1 kg) and triamcinolone (0.2 g) powders are mixed using a high-shear granulator at a constant speed. Stearic acid (20 g, 2% by weight) is metered into the raw testosterone and triamcinolone admixture in the high-shear mixer at a constant rate for a duration to form a powdery admixture.

An ethylcellulose (9 g) solution in ethanol is added to the powdery admixure at a constant rate to ensure even distribution. The wet binder results in the primary powder particles adhering to one another, thereby forming larger, multiparticle granules.

The wet granules are transferred into an oven and dried to remove the ethanol. The dried granules are transferred to a conical mill where the particle size of the granules pass through a round-hole conical mesh (0.018"/457.2 μm) to reduce their size. The milled particles are then mixed with stearic acid (20 g) in a low-shear mixer to allow the stearic acid to coat the granules. The granules are then processed with a rotary tablet press to form pellets. In one embodiment a 200 mg rectangular die is used to form the pellets. Compression is digitally monitored such that the resulting pellets have a hardness from about 50 to about 75 Newtons. The pellets are weighed periodically to ensure consistently accurate product.

Various process steps are undertaken in specific ways to obtain the final pellets having the correct hardness and dissolvability, thereby, the required bioavailability.

Granulation is conducted in a high-shear granulator at a constant speed for a pre-determined time as set by the formulator to match the final pellet properties. During this granulation step, the binder is metered into the composition at a constant rate while the granulator continues to spin.

Particle size reduction during the milling process is important for obtaining pellets having the desired physical characteristics. The size reduction is performed using a conical mill which passes the granules through a 457.2 mm (0.018") mesh at a constant speed.

In general, pellets are formed using either rectangular dies having various capacities, for example, 62.5 mg to 200 mg die or a circular die having 12.5 mg to 50 mg capacities. Once formed the tablets are pressed to obtain the desired hardness, for example, less than about 75 Newtons as described herein above.

What is claimed is:

1. An implantable pharmaceutical composition, consisting of:
   a) from about 10 mg to about 250 mg by weight of testosterone;
   b) from about 1 μg to about 50 μg by weight of triamcinolone; and
   c) from about 0.4 mg to about 12 mg of stearic acid, ethylcellulose or mixtures thereof.
2. The composition according to claim 1, consisting of:
   a) 200 mg of testosterone;
   b) 40 μg of triamcinolone; and
   c) 8 mg of stearic acid and 1.8 mg of ethylcellulose.
3. The composition according to claim 1, consisting of:
   a) 100 mg of testosterone;
   b) 20 μg of triamcinolone; and
   c) 4 mg of stearic acid and 0.9 mg of ethyl cellulose.
4. The composition according to claim 1, consisting of:
   a) 87.5 mg of testosterone;
   b) 17.5 μg of triamcinolone; and
   c) 3.5 mg of stearic acid and 0.788 mg of ethylcellulose.
5. The composition according to claim 1, consisting of:
   a) 62.5 mg of testosterone;
   b) 12.5 μg of triamcinolone; and
   c) 2.5 mg of stearic acid and 0.563 mg of ethylcellulose.
6. The composition according to claim 1, consisting of:
   a) 50 mg of testosterone;
   b) 10 μg of triamcinolone; and
   c) 2 mg of stearic acid and 0.45 mg of ethylcellulose.
7. The composition according to claim 1, consisting of:
   a) 37.5 mg of testosterone;
   b) 7.5 μg of triamcinolone; and
   c) 1.5 mg of stearic acid and 0.388 mg of ethyl cellulose.
8. The composition according to claim 1, consisting of:
   a) 25 mg of testosterone;
   b) 5 μg of triamcinolone; and
   c) 1 mg of stearic acid and 0.225 mg of ethyl cellulose.
9. The composition according to claim 1, consisting of:
   a) 12.5 mg of testosterone;
   b) 2.5 μg of triamcinolone; and
   c) 0.5 mg of stearic acid and 0.113 mg of ethylcellulose.
10. An implantable pharmaceutical composition, consisting of:
    a) about 95.3% by weight of testosterone;
    b) about 0.02% by weight of triamcinolone; and
    c) about 3.8% by weight of stearic acid and 0.86% by weight of ethyl cellulose.
11. A method for treating a subject in need of an increased testosterone level, comprising contacting the subject with a composition consisting of:
    a) from about 10 mg to about 250 mg by weight of testosterone;
    b) from about 1 μg to about 50 μg by weight of triamcinolone;
    c) from about 0.5 mg to about 12.5 mg by weight of stearic acid; and
    d) from about 0.113 mg to about 1.8 mg by weight of ethylcellulose.
12. The method according to claim 11, wherein the composition is consisting of:
    a) 200 mg of testosterone;
    b) 40 μg of triamcinolone; and
    c) 8 mg of stearic acid and 1.8 mg of ethylcellulose.
13. The method according to claim 11, wherein the composition is consisting of:
    a) 100 mg of testosterone;
    b) 20 μg of triamcinolone; and
    c) 4 mg of stearic acid and 0.9 mg of ethyl cellulose.
14. The method according to claim 11, wherein the composition is consisting of:
    a) 87.5 mg of testosterone;
    b) 17.5 μg of triamcinolone; and
    c) 3.5 mg of stearic acid and 0.788 mg of ethylcellulose.
15. The method according to claim 11, wherein the composition is consisting of:
    a) 62.5 mg of testosterone;
    b) 12.5 μg of triamcinolone; and
    c) 2.5 mg of stearic acid and 0.563 mg of ethylcellulose.
16. The method according to claim 11, wherein the composition is consisting of:
    a) 50 mg of testosterone;
    b) 10 μg of triamcinolone; and
    c) 2 mg of stearic acid and 0.45 mg of ethylcellulose.
17. The method according to claim 11, wherein the composition is consisting of:
    a) 37.5 mg of testosterone;
    b) 7.5 μg of triamcinolone; and
    c) 1.5 mg of stearic acid and 0.388 mg of ethyl cellulose.
18. The method according to claim 11, wherein the composition is consisting of:
    a) 25 mg of testosterone;
    b) 5 μg of triamcinolone; and
    c) 1 mg of stearic acid and 0.225 mg of ethyl cellulose.
19. The method according to claim 11, wherein the composition is consisting of:
    a) 12.5 mg of testosterone;
    b) 2.5 μg of triamcinolone; and
    c) 0.5 mg of stearic acid and 0.113 mg of ethylcellulose.
20. The method according to claim 11, wherein the subject is a male or a female.
21. The method according to claim 11, wherein the subject is a male.

22. The method according to claim 11, wherein the subject is a female.

* * * * *